United States Patent
Azam et al.

[11] Patent Number: 5,860,963
[45] Date of Patent: Jan. 19, 1999

[54] GUIDING CATHETER

[75] Inventors: Nusayr Azam, Minneapolis; John B. Logan, Plymouth; Brad J. Wessman, Crystal; William R. Priedeman, Wayzata, all of Minn.

[73] Assignee: Schneider (USA) Inc, Plymouth, Minn.

[21] Appl. No.: 751,342

[22] Filed: Nov. 19, 1996

Related U.S. Application Data

[63] Continuation of Ser. No. 165,127, Dec. 10, 1993, abandoned.

[51] Int. Cl.[6] .................................................... A61M 25/00
[52] U.S. Cl. .......................... 604/280; 604/282; 138/124; 138/138
[58] Field of Search ..................... 604/264, 280, 604/281–283, 93; 138/123, 124, 125, 137, 138, 140, 153; 600/433, 434, 435

[56] References Cited

U.S. PATENT DOCUMENTS

| | | |
|---|---|---|
| 3,585,707 | 6/1971 | Stevens . |
| 3,945,867 | 3/1976 | Heller, Jr. et al. . |
| 4,250,072 | 2/1981 | Flynn . |
| 4,282,876 | 8/1981 | Flynn . |
| 4,283,447 | 8/1981 | Flynn . |
| 4,345,602 | 8/1982 | Yoshimura et al. . |
| 4,425,919 | 1/1984 | Alston, Jr. et al. ................ 128/658 |
| 4,464,176 | 8/1984 | Wijayarathna . |
| 4,531,943 | 7/1985 | Van Tassel et al. . |
| 4,563,181 | 1/1986 | Wijayarathna et al. . |
| 4,596,563 | 6/1986 | Pande . |
| 4,636,346 | 1/1987 | Gold ...................................... 604/280 |
| 4,666,426 | 5/1987 | Aigner . |
| 4,739,768 | 4/1988 | Engelson . |
| 4,816,339 | 3/1989 | Tu et al. ................................. 623/66 |
| 4,817,613 | 4/1989 | Jaraczewski et al. . |
| 4,886,506 | 12/1989 | Lovgren et al. . |
| 4,898,591 | 2/1990 | Jang et al. . |
| 4,994,047 | 2/1991 | Walker et al. ...................... 604/280 |
| 5,045,072 | 9/1991 | Castillo et al. . |
| 5,061,257 | 10/1991 | Martinez et al. . |
| 5,078,702 | 1/1992 | Pomeranz .......................... 604/280 |
| 5,171,232 | 12/1992 | Castillo et al. . |
| 5,221,270 | 6/1993 | Parker . |
| 5,254,107 | 10/1993 | Soltesz . |
| 5,279,596 | 1/1994 | Castaneda et al. . |

FOREIGN PATENT DOCUMENTS

| | | |
|---|---|---|
| 1160531 | 1/1984 | Canada . |
| 0121215 | 10/1984 | European Pat. Off. . |
| 0473045 | 3/1992 | European Pat. Off. . |
| 0520692 | 12/1992 | European Pat. Off. . |
| 0542246A1 | 5/1993 | European Pat. Off. . |
| 9113648 | 9/1991 | WIPO . |
| 9215356 | 9/1992 | WIPO . |
| 9300953 | 1/1993 | WIPO . |

*Primary Examiner*—Ronald Stright
*Attorney, Agent, or Firm*—Peter C. Richardson; Lawrence C. Akers; Philip C. Strassburger

[57] ABSTRACT

A catheter is disclosed having a proximal shaft formed from an inner liner formed from a copolymer of polyvinylidene fluoride and hexafluoropropylene, an outer jacket formed from a blend of nylon and polyether block amide or polyether block amide alone, and a soft flexible tip affixed to the distal end of the proximal shaft formed from polyether block amide. A stem may be located between the proximal shaft and the soft flexible tip. The stem has an outer jacket formed from a proximal stem transition sleeve with a tapered distal end and a distal stem sleeve with a complementary tapered proximal end connected to the tapered distal end of the proximal stem transition sleeve. The stem transition sleeve and the stem sleeve are both formed from polyether block amide alone or a blend of polyether block amide and nylon. The outer jacket may be the same hardness as or harder than the stem transition sleeve which in turn is harder than the stem sleeve and the soft flexible tip. An intermediate wire mesh braid extends through the proximal shaft and, if desired, through the stem.

38 Claims, 2 Drawing Sheets

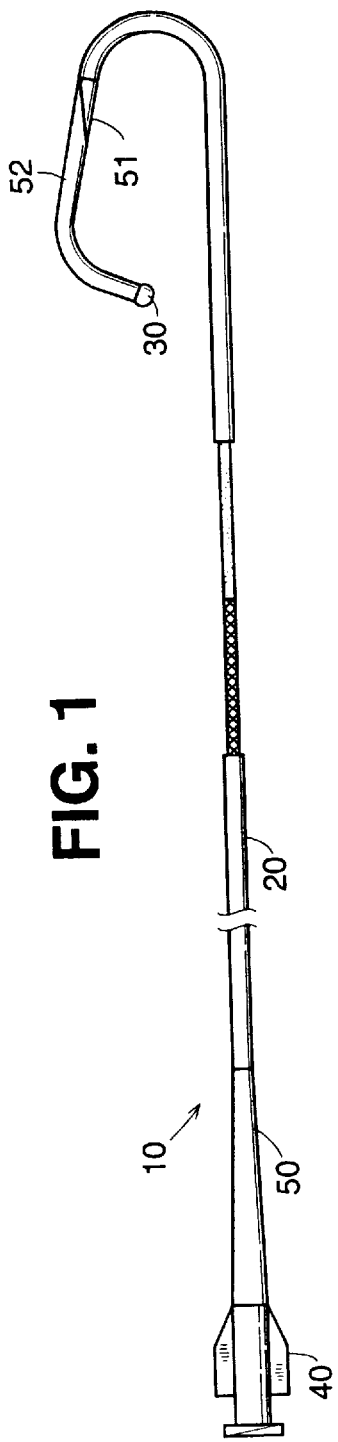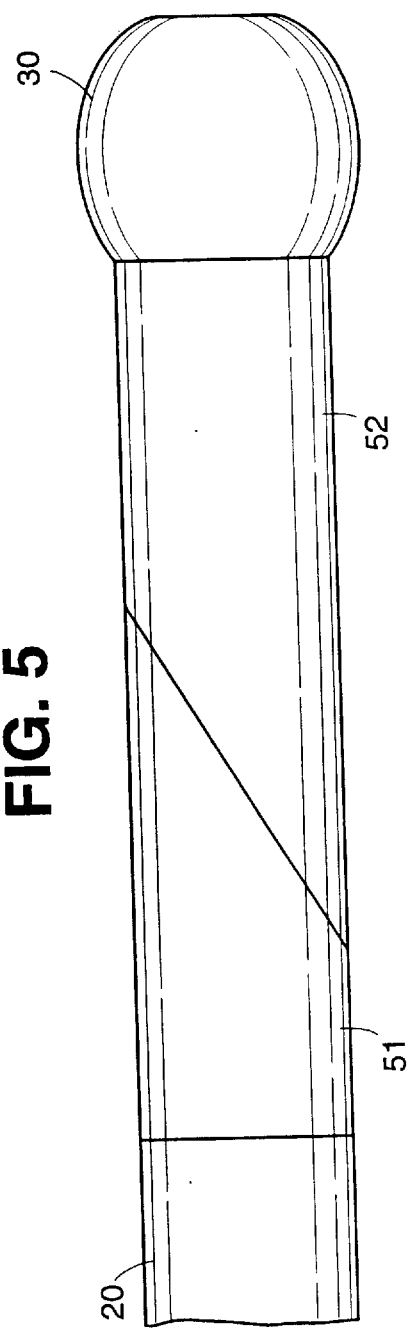

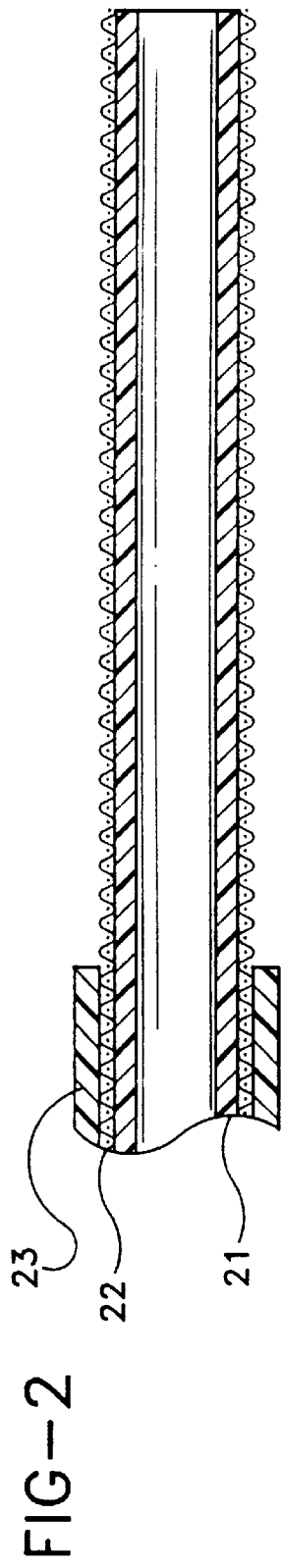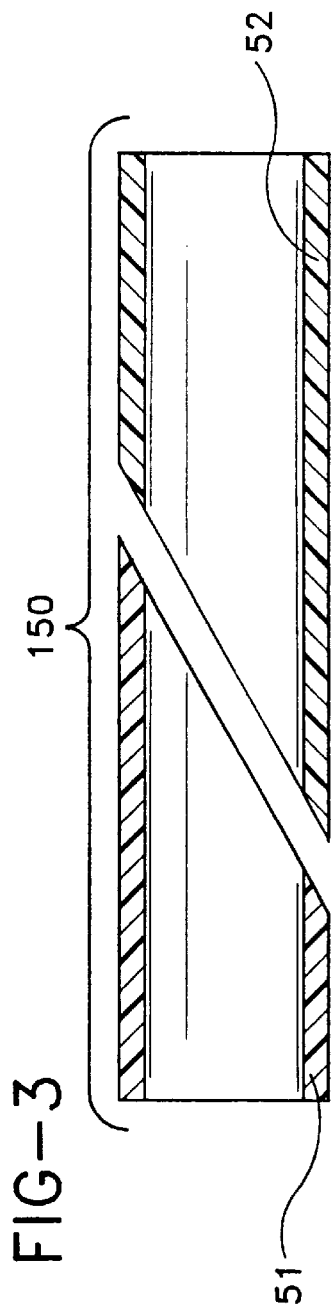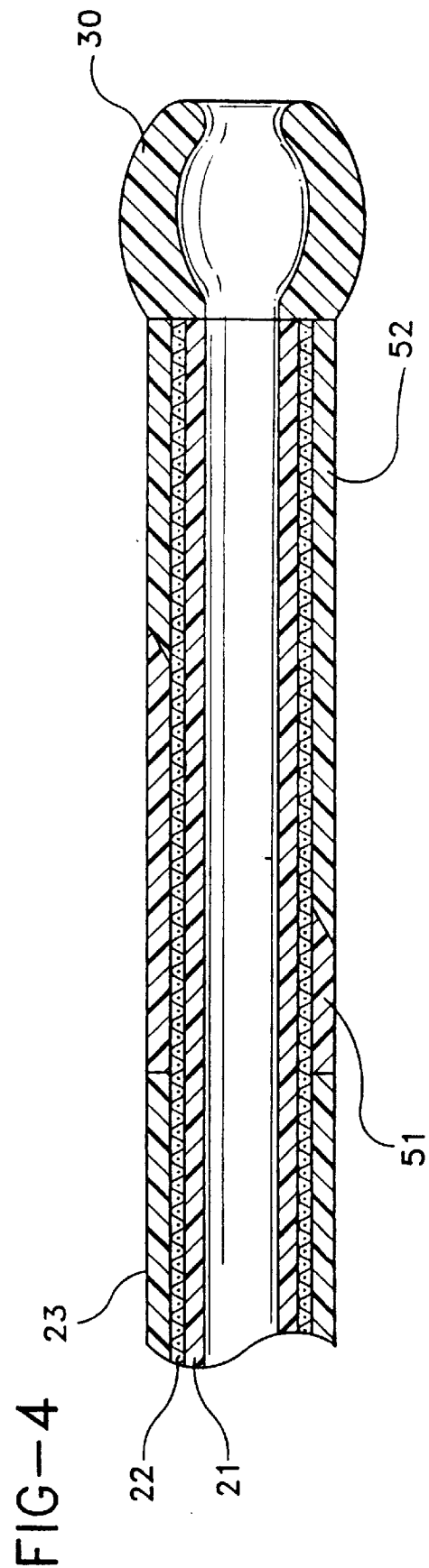

GUIDING CATHETER

This is a continuation of application Ser. No. 08/165,127 filed on Dec. 10, 1993, now abandoned.

BACKGROUND OF THE INVENTION

Guiding catheters are commonly used during coronary angioplasty procedures to aid in delivering a balloon catheter or other interventional medical device to a treatment site in a coronary vessel. In a routine coronary angioplasty procedure, a guiding catheter is introduced into a peripheral artery and advanced over a guidewire through the aorta until the distal end of the guiding catheter is engaged with the appropriate coronary ostium. Next a balloon dilatation catheter is introduced over the guidewire and through the guiding catheter. The guidewire is advanced past the distal end of the guiding catheter within the lumen of the diseased vessel and manipulated across the region of the stenosis. The balloon dilatation catheter is then advanced past the distal end of the guiding catheter over the guidewire until the balloon is positioned across the stenotic lesion. After the balloon is inflated to dilate the blood vessel in the region of the stenotic lesion, the guidewire, balloon dilatation catheter and guiding catheter are withdrawn.

Guiding catheters typically have preformed bends formed along their distal portion to facilitate placement of the distal end of the guiding catheter into the ostium of a particular coronary artery of a patient. In order to function efficiently, guiding catheters should have a relatively stiff main body portion and soft distal tip. This stiffness has been provided in the past by using a reinforced construction or by using certain relatively stiff polymeric materials. The stiff main body portion gives the guiding catheter sufficient "pushability" and "torqueability" to allow the guiding catheter to be inserted percutaneously into a peripheral artery, moved and rotated in the vasculature to position the distal end of the catheter at the desired site adjacent to a particular coronary artery. However, the distal portion should have sufficient flexibility so that it can track over a guidewire and be maneuvered through a tortuous path to the treatment site. In addition, a soft distal tip at the very distal end of the catheter should be used to minimize the risk of causing trauma to a blood vessel or even puncturing the vessel wall while the guiding catheter is being moved through the vasculature to the proper position. Such a soft tip is described in U.S. Pat. No. 4,531,943. In addition, the inner surface of the guiding catheter should be lubricous to facilitate movement of guidewires, balloon catheters and other interventional medical devices therethrough.

Guiding catheters currently on the market attempt to achieve these goals with varying degrees of success. However, none of the previous or current designs have heretofore provided an optimum combination of features that yield a catheter with a stiff main body portion, a flexible distal portion and a soft distal tip that can be successfully used in coronary angioplasty procedures.

Therefore it would be desirable to provide a guiding catheter that has sufficient rigidity along its proximal portion for enhanced pushability and torqueability, yet has a flexible distal portion and soft tip to provide enhanced trackability and minimize trauma to the vessel wall.

It would also be desirable to provide a guiding catheter that has a lubricous inner surface to facilitate movement of guidewires, balloon catheters and other interventional devices therethrough.

It would be further desirable to provide a guiding catheter that is easy to manufacture.

SUMMARY OF THE INVENTION

These and other objects are achieved by the guiding catheter of the present invention. This guiding catheter has a bodystock and a soft distal tip. The bodystock has an inner liner, an intermediate wire mesh braid and an outer jacket. The inner liner is formed from a copolymer of polyvinylidene fluoride (PVDF) and hexafluoropropylene (HFP). The outer jacket is made from a blend of nylon and polyether block amide (PEBA) or from PEBA alone. The soft distal tip is formed from PEBA and is injection molded onto the distal end of the bodystock.

The guiding catheter of this invention can also include a stem. The stem is comprised of a stem transition sleeve and a stem sleeve that fits over the inner liner along a distal portion of the bodystock. The stem transition sleeve has a tapered distal portion. The stem sleeve has a tapered proximal portion that complements the taper of the stem transition sleeve. The outer jacket of the bodystock along this distal portion is removed to allow the stem transition sleeve and stem sleeve to be fitted thereon. In addition, the stem may have a braided reinforcement therein.

BRIEF DESCRIPTION OF THE DRAWINGS

The above and other objects and advantages of this invention will be apparent upon consideration of the following detailed description, taken in conjunction with the accompanying drawings, in which like reference characters refer to like parts throughout and in which:

FIG. 1 is a plan view of one embodiment of the guiding catheter of this invention with a portion of the catheter removed to show the construction of the bodystock;

FIG. 2 is a longitudinal sectional view of the distal portion of one embodiment of the guiding catheter of this invention prior to the attachment of the stem and tip;

FIG. 3 is a longitudinal sectional view of the stem transition sleeve and stem sleeve prior to assembly of the guiding catheter of this invention;

FIG. 4 is a longitudinal sectional view of the distal portion of one embodiment of the guiding catheter of this invention; and FIG. 5 is a plan view of the distal portion of the guiding catheter of this invention showing the stem transition sleeve, stem sleeve and soft tip.

DETAILED DESCRIPTION OF THE INVENTION

One embodiment of the invention is a guiding catheter 10 which has a tubular bodystock 20 and a soft tip 30 attached to the distal end of bodystock 20. Guiding catheter 10 can have any desired inner diameter and outer diameter. Typical dimensions are an inner diameter of between about 0.050 inches to about 0.130 inches (0.127 cm to 0.330 cm) and an outer diameter of about 0.070 inches to about 0.150 inches (0.178 cm to 0.381 cm). A conventional polycarbonate hub 40 is attached to the proximal end of bodystock 20. In addition, an injection molded strain relief tube 50 is connected to hub 40 and the proximal portion of bodystock 20. Strain relief tube 50 preferably has a tapered design as shown in FIG. 1. However, a constant outside diameter construction could also be used. The material used to produce strain relief tube 50 is a polyether block amide (PEBA) having a hardness of 25 D to 63 D. The PEBA may be mixed with up to 50% nylon, preferably nylon-12, 15% to 36% barium sulfate for radiopacity and either 4% titanium dioxide or 0.5% organic pigment as a colorant.

Bodystock 20 is formed from an inner liner 21, an intermediate wire mesh braid 22 and an outer jacket 23. Inner liner 21 is formed from a copolymer of polyvinylidene fluoride (PVDF) and hexafluoropropylene (HFP). HFP is used to enhance the ability of inner liner 21 to be plasma etched to facilitate the attachment of outer jacket 23 thereto. Preferably 10% HFP is used. Suitable PVDF/HFP copolymer can be obtained from Solvay under the designation Solef. The PVDF/HFP copolymer preferably has a thickness of between about 0.0010 inches (0.0025 cm) and about 0.0050 inches (0.0127 cm).

Inner liner 21 when formed from a PVDF/HFP copolymer provides a lubricous surface facing the lumen of guiding catheter 10. This facilitates the passage of other medical devices therethrough. In addition, the use of a PVDF/HFP copolymer for inner liner 21 allows guiding catheter to be gamma sterilized. Other prior catheters that use a polytetrafluoroethylene (PTFE/Teflon) inner liner cannot be gamma sterilized because PTFE is not gamma stable. If gamma sterilization will not be used, PVDF could be combined with another polymer such as PTFE. In addition, the PVDF/HFP copolymer can be extruded continuously. This contributes to the ease of manufacture of the resulting product.

Intermediate wire mesh braid 22 is formed from stainless steel wires braided over inner liner 21. Although stainless steel wire is preferred, other suitable materials such as Kevlar, or various polymer filaments could also be used. The stainless steel wire has a circular cross-section with a diameter of between about 0.0010 inches (0.0025 cm) and about 0.0030 inches (0.0076 cm). Alternatively, a flat wire could be used. Any suitable braid pattern can be used for intermediate wire mesh braid 22. Preferably a 16 wire stagger braid pattern is used. In this pattern each wire is helically wound around inner liner 21 in a two over and two under braided manner. The braid angle, as measured from the plane perpendicular to the longitudinal axis of guiding catheter 10, can be between about 15 degrees and about 60 degrees with 30 degrees being preferred.

Outer jacket 23 is formed from PEBA alone or from a blend of PEBA and nylon. Suitable PEBA can be obtained from Atochem under the designation Pebax. Suitable nylon can be obtained from Huls, America under the designation Vestamid. Outer jacket 23 preferably has a durometer of between about 63 D and about 72 D. When a blend of nylon and PEBA is used for outer jacket 23, preferably up to 50% nylon-12 is used. The use of PEBA alone or blended with nylon provides a bodystock material that is sufficiently stiff so that guiding catheter 10 has a proximal portion with enhanced "pushability" and "torqueability".

Optionally the PEBA or nylon and PEBA blend for outer jacket 23 can be mixed with a radiopaque material. Suitable materials are barium sulfate, bismuth subcarbonate, bismuth trioxide and bismuth oxychloride. Preferably a 36% by weight loading of barium sulfate is used. Lesser or greater amounts of barium sulfate can be used to make outer jacket 23 less radiopaque or more radiopaque as the case may be. A pigment can also be used to color outer jacket 23. If such a pigment is used, preferably 0.5% by weight is used. Lesser or greater amounts of the pigment can be used depending on the color desired.

Soft tip 30 constitutes the most distal end of guiding catheter 10. It is formed from PEBA such as the PEBA used for outer jacket 23. Preferably soft tip 30 has a durometer of between about 25 D and about 40 D. This gives soft tip 30 a softness that is sufficient to minimize the chances of damage to the inner surface of a blood vessel through which guiding catheter 10 may pass. In addition, it is hard enough to maintain an opening therethrough to allow the passage of a guidewire, balloon catheter or other interventional medical device to pass out of the distal end of soft tip 30. Soft tip 30 can be made radiopaque by mixing 15% by weight barium sulfate with the PEBA. Of course greater or lesser amounts of barium sulfate or other radiopaque filler can be used. A 4% by weight loading of titanium dioxide can be used to color soft tip 30. Again greater or lesser amounts of titanium dioxide can be used. Preferably soft tip 30 has a length of between about 0.060 inches (0.15 cm) to about 0.20 (0.51 cm) inches.

Preferably guiding catheter 10 has a stem 150 located between bodystock 20 and soft tip 30. Stem 150 is composed of stem transition sleeve 51 and a stem sleeve 52. Stem transition sleeve 51 is formed from 40 D to 70 D PEBA blended with up to 50% nylon by weight. In addition, 36% barium sulfate by weight and 0.5% by weight of an organic pigment can be used. Again greater or lesser amounts of barium sulfate and the pigment can be used. Stem sleeve 52 is formed from 25 D to 40 D PEBA with up to 50% by weight of nylon. In addition, 15% to 36% by weight of barium sulfate can be used. Finally, 4% by weight of titanium dioxide or 0.5% by weight of an organic pigment can be used to provide color to stem sleeve 52. Again greater or lesser amounts of barium sulfate and the pigment can be used.

Stem transition sleeve 51 has a taper along the distal portion. Preferably this taper is 20 degrees but can be from about 10 degrees to about 30 degrees. Stem sleeve 52 has a complementary taper along its proximal portion to provide a smooth transition between stem transition sleeve 51 and stem sleeve 52. The length of stem sleeve 52 can vary depending on the length of the distal portion of guiding catheter 10 that is desired to be flexible. Preferably stem sleeve 52 can be from about 0.45 inches (1.14 cm) to about 2.1 inches (5.33 cm) as measured from its most distal end to the most proximal end of the taper. In addition, stem 150 can have a total length of between about 0.5 inches (1.27 cm) to about 6 inches (15.24 cm).

Stem transition sleeve 51 and stem sleeve 52 fit over the distal portion of bodystock 20 where outer jacket 23 and, if desired, braid 22 have been removed. This configuration provides a smooth transition in the flexibility of guiding catheter 10 from its proximal end to its distal end. This smooth transition from the high hardness/stiffness of bodystock 20 to the high softness of soft tip 30 eliminates stress concentration at the stem to bodystock joint. High stress concentrations at this joint would promote kinking and failure of guiding catheter 10.

Guiding catheter 10 can be manufactured according to the following process. A thin layer of PVDF/HFP copolymer is extruded over a silicone impregnated acetal core rod to form inner liner 21. The PVDF/HFP copolymer is plasma etched in an argon/oxygen atmosphere. Other atmospheres, such as an ammonia atmosphere, could also be used. Preferably a molar ratio of 70 to 30 argon to oxygen is excited by an electrical current of 550 watts in a vacuum of 200 millitorr. The residence time of inner jacket 21 is six minutes. This gas plasma chemically modifies the surface of the copolymer as it passes through the plasma field. This surface modification leaves active molecular bonding sites free to attach to the polymer molecules in the second jacket. Of course this surface modification could be achieved by chemically etching the copolymer with, for example, butyl amine. The plasma etching step can occur either before or after the braiding step. A plurality of stainless steel wires are braided around the PVDF/HFP inner liner 21. The number of wires used is a function of the diameter of the catheter to be formed and the desired rigidity for the catheter. The PEBA or nylon/PEBA blend outer jacket 23 is extruded over wire mesh braid 22. For the stemless embodiment, the distal end of the resulting assembly is ground and soft tip 30 is injection molded thereto.

In the stemmed embodiment, a distal portion of outer jacket 23 and, if desired, a corresponding length of braid 22 is removed. Then a pre-extruded stem transition sleeve 51 and a pre-extruded stem sleeve 52 are slipped over the distal portion and RF welded in place. Soft tip 30 is injection molded to the distal end of this assembly.

Thus it is seen that a guiding catheter is provided that has a lubricous inner surface and is sufficiently rigid along its proximal length to provide "pushability" and "torqueability" yet is flexible along its distal portion and has a distal soft tip to provide enhanced trackability and to minimize trauma to the vessel wall. One skilled in the art will appreciate that the described embodiments are presented for purposes of illustration and not of limitation and the present invention is only limited by the claims which follow.

We claim:

1. A catheter comprising:
   an elongate proximal tube having a proximal end and a distal end with an exposed innermost liner formed from a material consisting essentially of a copolymer of polyvinylidene fluoride and hexafluoropropylene, an intermediate reinforcing layer and an outer jacket formed from a material including a blend of nylon and polyether block amide or polyether block amide alone; and
   a soft flexible tip formed from a material including polyether block amide affixed to the distal end of the elongate proximal tube;
   wherein the catheter is stable upon exposure to gamma radiation.

2. The catheter of claim 1 wherein the material forming the outer jacket is harder than the material forming the soft flexible tip.

3. The catheter of claim 2 wherein the material forming the outer jacket has a hardness in the range of about 63 D to about 72 D and the material forming the soft flexible tip has a hardness in the range of about 25 D to about 40 D.

4. The catheter of claim 3 wherein the intermediate reinforcing layer is a wire mesh braid.

5. The catheter of claim 2 wherein the intermediate reinforcing layer is a wire mesh braid.

6. The catheter of claim 1 wherein the intermediate reinforcing layer is a wire mesh braid.

7. The catheter of claim 1 wherein the catheter is sterilized by exposure to gamma radiation.

8. The catheter of claim 1 wherein the catheter is devoid of polytetrafluoroethylene.

9. A catheter comprising:
   an elongate tube having a proximal end and a distal end defining an inner lumen and a wall with an annular cross section of a substantially uniform thickness between the distal end and the proximal end and with an exposed innermost liner formed from a material consisting essentially of a copolymer of polyvinylidene fluoride and hexafluoropropylene and an outer polymeric jacket;
   wherein the catheter is stable upon exposure to gamma radiation.

10. The catheter of claim 9 wherein the inner liner has a thickness of between about 0.001 inches (0.0025 cm) and about 0.005 inches (0.0127 cm).

11. The catheter of claim 10 wherein the catheter further includes a soft flexible tip formed from a material including polyether block amide affixed to the distal end of the elongate tube.

12. The catheter of claim 9 wherein the catheter further includes a soft flexible tip formed from a material including polyether block amide affixed to the distal end of the elongate tube.

13. The catheter of claim 9 wherein the catheter is sterilized by exposure to gamma radiation.

14. The catheter of claim 9 wherein the catheter is devoid of polytetrafluoroethylene.

15. A catheter comprising:
    an elongate proximal tube having a proximal end and a distal end with an exposed innermost inner liner formed from a material including a copolymer of polyvinylidene fluoride and hexafluoropropylene, an intermediate reinforcing layer and an outer jacket formed from a material including a blend of nylon and polyether block amide or polyether block amide alone; and
    a soft flexible tip formed from a material including polyether block amide affixed to the distal end of the elongate proximal tube;
    wherein the catheter is stable upon exposure to gamma radiation.

16. The catheter of claim 15 wherein the material forming the outer jacket has a hardness in the range of about 63 D to about 72 D and the material forming the soft flexible tip has a hardness in the range of about 25 D to about 40 D.

17. The catheter of claim 15 wherein the intermediate reinforcing layer is a wire mesh braid.

18. The catheter of claim 15 wherein the inner liner consists essentially of a copolymer of polyvinylidene fluoride and hexafluoropropylene.

19. The catheter of claim 15 wherein the catheter is sterilized by exposure to gamma radiation.

20. The catheter of claim 15 wherein the catheter is devoid of polytetrafluoroethylene.

21. A catheter comprising:
    an elongate tube having a proximal end and a distal end defining an inner lumen and a wall with an annular cross section of a substantially uniform thickness between the distal end and the proximal end and with an exposed innermost liner formed from a material including a copolymer of polyvinylidene fluoride and hexafluoropropylene and an outer polymeric jacket;
    wherein the catheter is stable upon exposure to gamma radiation.

22. The catheter of claim 21 wherein the inner liner has a thickness of between about 0.001 inches (0.0025 cm) and about 0.005 inches (0.0127 cm).

23. The catheter of claim 21 wherein the catheter further includes a soft flexible tip formed from a material including polyether block amide affixed to the distal end of the elongate tube.

24. The catheter of claim 21 wherein the inner liner consists essentially of a copolymer of polyvinylidene fluoride and hexafluoropropylene.

25. The catheter of claim 21 wherein the catheter is sterilized by exposure to gamma radiation.

26. The catheter of claim 21 wherein the catheter is devoid of polytetrafluoroethylene.

27. A catheter comprising:

an elongate proximal tube having a proximal end and a distal end with a plasma etched exposed innermost liner formed from a material including a copolymer of polyvinylidene fluoride and hexafluoropropylene, an intermediate reinforcing layer, and an outer jacket formed from a material including a blend of nylon and polyether block amide or polyether block amide alone; and a soft flexible tip formed from a material including polyether block amide affixed to the distal end of the elongate proximal tube;

wherein the catheter is stable upon exposure to gamma radiation.

28. The catheter of claim 27 wherein the material forming the outer jacket has a hardness in the range of about 63 D to about 72 D and the material forming the soft flexible tip has a hardness in the range of about 25 D to about 40 D.

29. The catheter of claim 27 wherein the intermediate reinforcing layer is a wire mesh braid.

30. The catheter of claim 27 wherein the inner liner consists essentially of a copolymer of polyvinylidene fluoride and hexafluoropropylene.

31. The catheter of claim 27 wherein the catheter is sterilized by exposure to gamma radiation.

32. The catheter of claim 27 wherein the catheter is devoid of polytetrafluoroethylene.

33. A catheter comprising:

an elongate tube having a proximal end and a distal end defining an inner lumen and a wall with an annular cross section of a substantially uniform thickness between the distal end and the proximal end and with a plasma etched exposed innermost liner formed from a material including a copolymer of polyvinylidene fluoride and hexafluoropropylene and an outer polymeric jacket;

wherein the catheter is stable upon exposure to gamma radiation.

34. The catheter of claim 33 wherein the inner liner has a thickness of between about 0.001 inches (0.0025 cm) and about 0.005 inches (0.0127 cm).

35. The catheter of claim 33 wherein the catheter further includes a soft flexible tip formed from a material including polyether block amide affixed to the distal end of the elongate tube.

36. The catheter of claim 33 wherein the inner liner consists essentially of a copolymer of polyvinylidene fluoride and hexafluoropropylene.

37. The catheter of claim 33 wherein the catheter is sterilized by exposure to gamma radiation.

38. The catheter of claim 33 wherein the catheter is devoid of polytetrafluoroethylene.

* * * * *